United States Patent [19]

Gresl, Jr.

[11] Patent Number: 5,318,580

[45] Date of Patent: Jun. 7, 1994

[54] RETRACTABLE TROCAR

[75] Inventor: Charles Gresl, Jr., San Francisco, Calif.

[73] Assignee: Origin Medsystems, Inc., Menlo Park, Calif.

[21] Appl. No.: 752,867

[22] Filed: Aug. 30, 1991

Related U.S. Application Data

[63] Continuation-in-part of Ser. No. 580,766, Sep. 11, 1990, abandoned.

[51] Int. Cl.⁵ .............................................. A61B 17/32
[52] U.S. Cl. .................................. 606/185; 604/164; 604/167
[58] Field of Search ................ 604/192, 194–198, 604/110, 263, 262, 164, 165, 166, 169, 170, 272, 274, 167, 264; 606/167, 185, 184; 206/365, 366

[56] References Cited

U.S. PATENT DOCUMENTS

| Re. 32,922 | 5/1989 | Levin et al. . | |
|---|---|---|---|
| 1,248,492 | 12/1917 | Hill . | |
| 2,001,638 | 5/1935 | Tornsjo . | |
| 2,623,521 | 12/1952 | Shaw . | |
| 2,630,803 | 3/1953 | Baran . | |
| 3,713,447 | 1/1973 | Adair . | |
| 3,994,287 | 11/1976 | Turp et al. . | |
| 4,254,762 | 3/1981 | Yoon . | |
| 4,256,119 | 3/1981 | Gauthier | 128/754 |
| 4,360,016 | 11/1982 | Sarrine | 128/763 |
| 4,442,836 | 4/1984 | Meinecke et al. . | |
| 4,449,529 | 5/1984 | Burns et al. . | |
| 4,499,898 | 2/1985 | Knepshield et al. . | |
| 4,517,978 | 5/1985 | Levin et al. . | |
| 4,527,561 | 7/1985 | Burns . | |
| 4,535,773 | 8/1985 | Yoon . | |
| 4,559,041 | 12/1985 | Razi | 604/157 |
| 4,601,710 | 7/1986 | Moll . | |
| 4,654,030 | 3/1987 | Moll et al. . | |
| 4,747,831 | 5/1988 | Kulli | 604/110 |
| 4,776,346 | 10/1988 | Beraha et al. | 128/754 |
| 4,808,168 | 2/1989 | Warring . | |
| 4,813,426 | 3/1989 | Haber et al. | 128/763 |
| 4,817,631 | 4/1989 | Schnepp-Pesch et al. . | |
| 4,850,961 | 7/1989 | Wanderer et al. . | |
| 4,895,147 | 1/1990 | Bodicky et al. . | |
| 4,902,280 | 2/1990 | Lander . | |
| 4,911,693 | 3/1990 | Paris | 604/192 |
| 4,931,042 | 6/1990 | Holmes et al. . | |
| 4,943,280 | 7/1990 | Lander . | |
| 4,973,316 | 11/1990 | Dysarz | 604/195 |

(List continued on next page.)

FOREIGN PATENT DOCUMENTS

| 0293123 | 5/1988 | European Pat. Off. . |
|---|---|---|
| 0312219 | 9/1988 | European Pat. Off. . |
| 0349955 | 1/1990 | European Pat. Off. . |
| 0370733 | 5/1990 | European Pat. Off. . |
| 0378095 | 7/1990 | European Pat. Off. . |
| 0350291 | 10/1990 | European Pat. Off. . |
| 0413493A3 | 2/1991 | European Pat. Off. . |
| 0430594A1 | 6/1991 | European Pat. Off. . |
| 0432363A3 | 6/1991 | European Pat. Off. . |
| 0433581A3 | 6/1991 | European Pat. Off. . |

(List continued on next page.)

OTHER PUBLICATIONS

Russian Publication Entitled: "Needle for Puncture and Lavage of Abdominal Cavity." F. S. Zubairov. (translation included).

Primary Examiner—C. Fred Rosenbaum
Assistant Examiner—Anthony Gutowski
Attorney, Agent, or Firm—Limbach & Limbach

[57] ABSTRACT

A trocar is received in a trocar tube for movement relative to the tube between a position extended from the tube for piercing and a retracted position shielded by the tube. The trocar is mounted within a housing which carries a spring normally biasing the trocar to the retracted position. A latch mechanism within the housing is engageable with the trocar to maintain the trocar in the extended position. The latch mechanism senses the application of piercing force to the trocar and, upon the interruption of such force in response to the completion of a piercing operation, functions to release the trocar for retraction by the spring.

29 Claims, 6 Drawing Sheets

U.S. PATENT DOCUMENTS

| | | | |
|---|---|---|---|
| 4,994,042 | 2/1991 | Vadher | 604/165 |
| 5,009,643 | 4/1991 | Reich et al. | |
| 5,030,206 | 7/1991 | Lander | |
| 5,046,508 | 9/1991 | Weissler | 128/763 |
| 5,049,136 | 9/1991 | Johnson | 604/198 |
| 5,053,016 | 10/1991 | Lander | |
| 5,057,082 | 10/1991 | Burchette, Jr. | |
| 5,059,184 | 10/1991 | Dyke | 604/198 |
| 5,066,288 | 11/1991 | Deniega et al. | |
| 5,092,853 | 3/1992 | Couvertier | 604/195 |
| 5,104,382 | 4/1992 | Brinkerhoff et al. | 604/165 |
| 5,114,407 | 5/1992 | Burbank | 604/164 |
| 5,116,353 | 5/1992 | Green | 606/184 |
| 5,122,122 | 6/1992 | Allgood | 604/174 |
| 5,152,754 | 10/1992 | Plyley et al. | 604/164 |

FOREIGN PATENT DOCUMENTS

| | | |
|---|---|---|
| 0450111A1 | 10/1991 | European Pat. Off. |
| 0450886A1 | 10/1991 | European Pat. Off. |
| 0461568A1 | 12/1991 | European Pat. Off. |
| 3915597C1 | 5/1990 | Fed. Rep. of Germany |
| 3918431C1 | 7/1990 | Fed. Rep. of Germany |
| 4002235A1 | 8/1990 | Fed. Rep. of Germany |
| 3915215A1 | 11/1990 | Fed. Rep. of Germany |
| 3923243A1 | 1/1991 | Fed. Rep. of Germany |
| 4020956A1 | 1/1991 | Fed. Rep. of Germany |
| WO89/03661 | 5/1989 | PCT Int'l Appl. |
| WO91/08712 | 6/1991 | PCT Int'l Appl. |
| 475215 | 10/1952 | Spain |
| 921554 | 4/1982 | U.S.S.R. |
| 2240926 | 8/1991 | United Kingdom |

RETRACTABLE TROCAR

This is a continuation-in-part of application Ser. No. 580,766 filed Sep. 11, 1990, now abandoned.

FIELD OF THE INVENTION

The present invention relates to a trocar and, more particularly, is concerned with a trocar incorporating means to shield the obturating tip of the trocar immediately after it has achieved its piercing function. In its more specific aspects, the invention is concerned with such a means which does not rely on the interposition of a separate shielding tube or require a mechanism for moving such a tube.

BACKGROUND OF THE INVENTION

Trocars are pointed surgical instruments which puncture tissue to obtain access to body cavities. Inherent with such instruments is the danger that after the intended puncture, the trocar will inadvertently puncture unintended tissue, vessels or organs.

The prior art teaches various techniques for providing needles and trocars with means to avoid inadvertent puncturing. For example, hollow Veress needles are provided with spring-loaded internal pins which pop out beyond the sharp cutting end of the needles after the intended puncture has been completed. A more recent type of shielding used with trocars may be seen in U.S. Pat. Nos. 4,601,710 and 4,654,030, wherein the shielding takes the form of a sleeve which extends around the point of the trocar after piercing is complete. Both of these techniques require that something project beyond the piercing point of the needle or trocar, and require the addition of a separate shielding element.

The prior art also teaches trocars which are provided with trocar tubes received around the trocar so as to leave a passage extending into the body cavity after the trocar is removed. U.S. Pat. Nos. 4,601,710 and 4,654,030 both teach such tubes. In the case of these patents, however, a shielding sleeve, in addition to the tubes, is required. This necessarily increases the bulk of the trocar and adds to the complexity of its mechanism. Projecting a shielding sleeve beyond the end of the trocar also, necessarily, results in an additional element being extended beyond the tip of the trocar and into the body cavity. While this sleeve performs a shielding function while within the cavity, it would be ideal if the pointed tip of the trocar could be shielded without the necessity of extending yet another element into the body cavity.

U.S. Pat. No. 4,535,773 teaches techniques for shielding the sharp tip of a trocar through either the interposition of an extendable shielding sleeve, or the retraction of the trocar into the trocar tube. The latter arrangement is seen in the embodiment of FIGS. 34 and 35 of the patent. It relies upon a solenoid-operated detent which holds the trocar in the extended position relative to the trocar tube and requires electronic sensing means in the tip of the trocar to activate the detent for release. This sensing means requires an electronic alarm network.

SUMMARY OF THE INVENTION

The trocar of the present invention is received within a trocar tube for movement relative to the tube between a position extended from the tube for piercing, and a retracted position shielded by the tube. The trocar is mounted on a primary housing for movement between the extended and retracted positions. Biasing means carried by the housing normally urges the trocar to the retracted position. Latch means is provided within the housing for engagement with the trocar to maintain the trocar in the extended position. The latch means is responsive to the application of piercing force to the trocar and functions to release the trocar for retraction by the biasing means upon the interruption of such force.

A principal object of the present invention is to provide a trocar which is shielded to prevent inadvertent piercing immediately after the intended puncture is complete.

Yet another object of the invention is to provide such a trocar which is shielded without the interposition of a separate shielding sleeve.

Still another object of the invention is to provide such a trocar which is shielded by retraction of the trocar relative to the trocar tube.

A further object of the invention is to provide such a trocar which is automatically retracted within the trocar tube upon the completion of the intended puncture, without the requirement of electronic sensors.

Another object is to provide such a trocar which has a pushbutton mechanism for opening a spring-biased valve which seals the trocar tube housing subsequent to removal of the trocar.

Still another and more general object of the invention is to provide such a trocar which is of simplified construction and has a minimum of bulk.

A further object of the invention is to provide such a trocar wherein the shielding function is totally automatic and achieved in a simple manner which requires no special expertise on the part of the user.

Another general object of the invention is to provide a simplified mechanism to retract a trocar into the trocar tube within which it is received, after the trocar has penetrated through a layer of tissue and there is no longer any force being applied to the trocar by resistance to penetration.

The foregoing and other objects will become more apparent when viewed in light of the following detailed description and accompanying drawings.

DESCRIPTION OF THE PREFERRED EMBODIMENT

Figure 1:
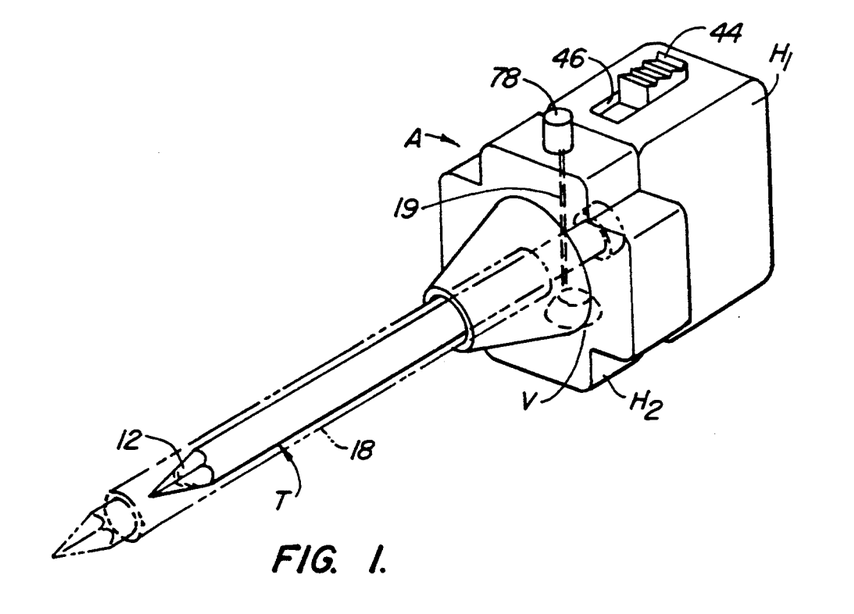
FIG. 1 is a perspective view of the inventive trocar assembly, with solid lines showing the trocar retracted, and phantom lines showing the trocar extended from a trocar tube.
Figure 2:
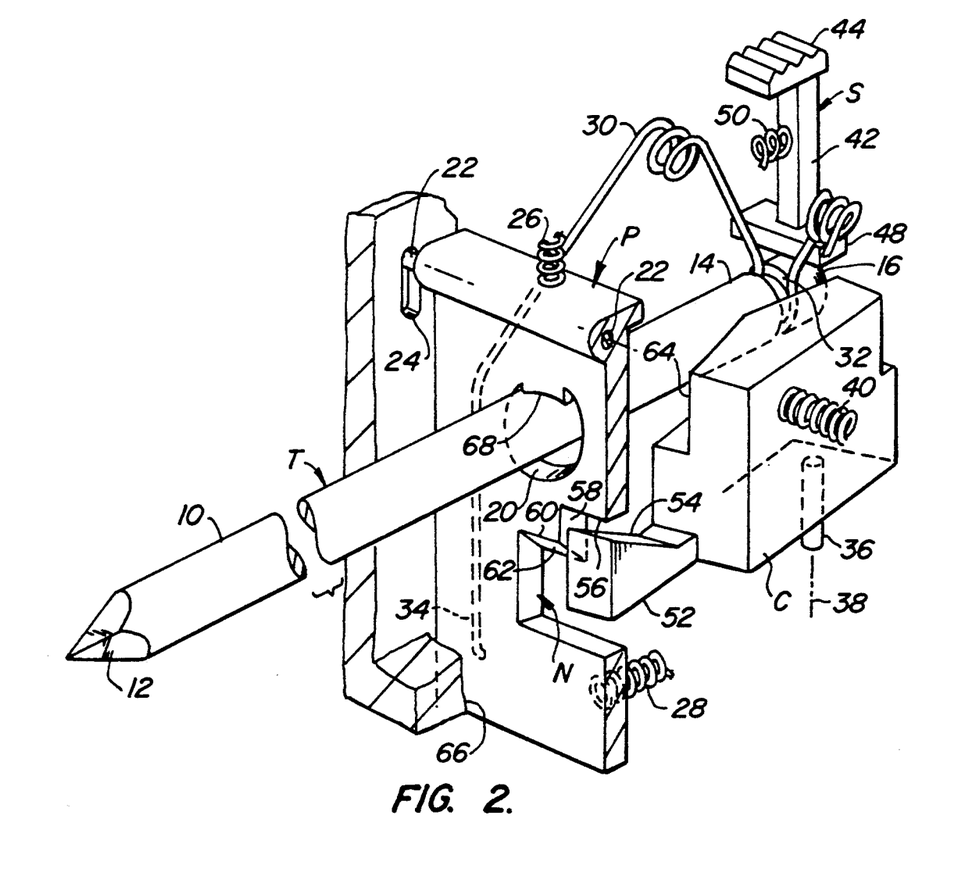
FIG. 2 is an enlarged perspective view, with parts thereof broken away, showing the internal construction of the mechanism within the primary housing for the trocar assembly, with the trocar in the retracted position.
Figures 3, 4, 5:
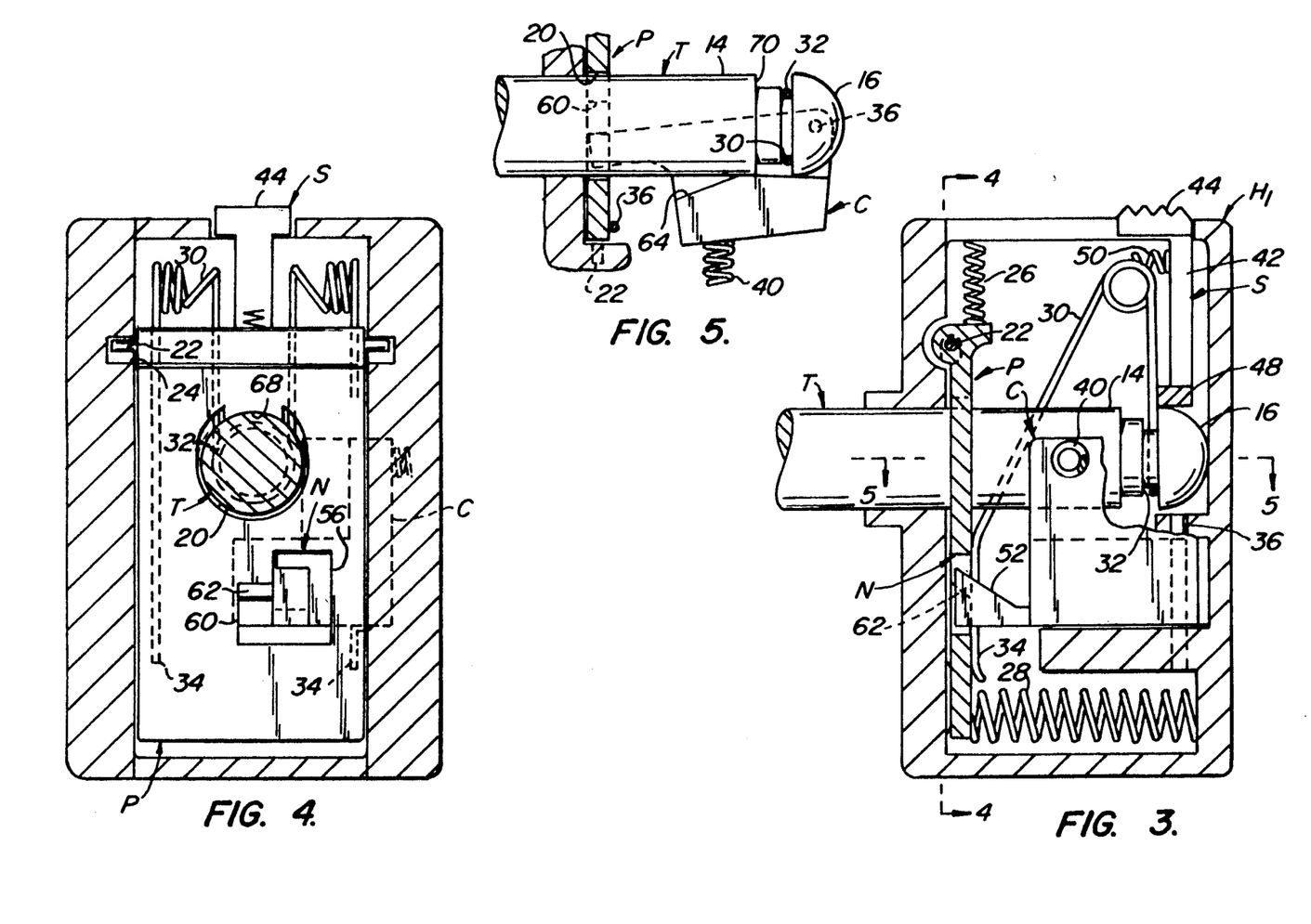
FIG. 3 is a cross-sectional side elevational view through the primary housing for the trocar assembly, illustrating the internal construction of the mechanism within the housing, with the trocar in the retracted position.
FIGS. 4 and 5 are cross-sectional views taken on the planes designated by lines 4—4 and 5—5, respectively, of FIG. 3.

As shown in FIGS. 1 and 2, the trocar assembly is designated in its entirety by the letter "A." Its basic elements comprise: a trocar "T" having a distal portion 10 terminating in a pointed tip or obturator 12 and a proximal portion 14 terminating in a hemispherical end 16; a primary base member or housing "H$_1$" slidably receiving the trocar for movement between extended and retracted positions; a secondary base member or housing "H$_2$" slidably received on the trocar "T" for mutual engagement with the housing "H$_1$," and a trocar tube 18 mounted on the housing "H$_2$" and slidably received on the trocar "T." The secondary housing "H$_2$" and trocar tube 18 are removable from the trocar "T" and primary housing "H$_1$" and, in use, are left in place in a puncture formed by the trocar to provide access to the interior of a body cavity.

A spring-biased flapper valve mechanism "V" is mounted in the secondary housing "H$_2$" to close the passage through the mechanism, and in turn the passage through the trocar tube 18, when the trocar is removed from the tube. A release plunger 78 extends to the outside of the housing "H$_2$" to manually open the valve "V," as will be more fully described.

A latching mechanism within the primary housing "H$_1$" receives the trocar "T" for slidable movement between the retracted and extended positions. This mechanism comprises: a plate "P" having an oblong aperture 20 formed therein for receiving the trocar; pins 22 supporting the plate "P" for pivotal and slidable movement relative to grooves 24 formed in the housing "H$_1$"; a plate engaging spring 26 interposed between the housing "H$_1$" and the top of the plate "P" to normally urge the plate downwardly (as viewed in FIG. 2); a plate disengaging spring 28 interposed between the housing and the bottom of the plate "P" to normally urge the plate in a clockwise forward direction (as viewed in FIG. 2); a "mousetrap-like" trocar spring 30 having a generally U-shaped central section received in an annular groove 32 formed around the proximal portion 14 of the trocar and distal end portions 34 bearing against the plate "P" to normally bias the trocar rearwardly to the retracted position and the plate "P" forwardly in a clockwise direction (as viewed in FIG. 2); a cam arm "C" pivotally mounted to the primary housing "H$_1$" by a pin 36 for movement about an upright vertical axis 38 (as viewed in FIG. 2); and a cam arm spring 40 interposed between the cam arm "C" and the primary housing "H$_1$" to normally urge the cam arm in a clockwise direction (as viewed in FIG. 2).

In the preferred embodiment, the mechanism also includes a slide "S" slidably received within the primary housing "H$_1$" to selectively move the trocar "T" to the extended position. The slide comprises a central body section 42 having a serrated knob 44 on its upper end slidably received within a slot 46 in the housing "H$_1$," and a foot 48 at its lower end disposed for engagement with the spring 30. The slide "S" is normally urged rearwardly (as viewed in FIG. 2) by a compression coil spring 50 interposed between the slide and the primary housing "H$_1$."

The cam arm "C" is formed with a cam extension 52 having a sloped cam surface 54. A stepped notch "N" is formed in the plate "P" for receiving the extension 52. The notch "N" comprises an enlarged section 56 adapted to loosely receive the extension 52 and having a side surface 58 against which the arm may slidably abut under the influence of the cam arm spring 40, and a reduced height lateral section 60 having an upper cam surface 62 mutually engageable with the cam surface 54 when the extension 52 is received within the section 60 (see FIGS. 8 to 14).

The cam arm "C" is notched on one of its sides, and formed with a lateral cam surface 64 positioned for sliding engagement with the hemispherical end 16 of the trocar when the trocar moves to the retracted position (shown in FIG. 2). Engagement of the hemispherical end 16 with the cam surface 64 functions to turn the cam arm "C" in a counterclockwise direction (as viewed in FIG. 2) against the force of the spring 40. This movement, in turn, functions to move the cam extension 52 into the enlarged section 56 of the notch "N."

FIG. 2 shows the trocar assembly with the latching plate "P" pivoted fully forward under the influence of the spring 28 into abutting engagement with a stop surface 66 formed on the housing "H₁." As there shown, it will be seen that an arcuate detent extension 68 is formed on the plate "P" and extends into slidable engagement with the top of the trocar "T" under the influence of the spring 26. A detent groove having a shoulder 70 is formed in the proximal portion of the trocar "T" for receiving the extension when the trocar is in the extended condition (see FIG. 6). Upon such receiving, the spring 26 functions to urge the plate "P" downwardly, thus engaging the extension 68 with the shoulder 70 and locking the trocar in the extended condition.

Figure 18:
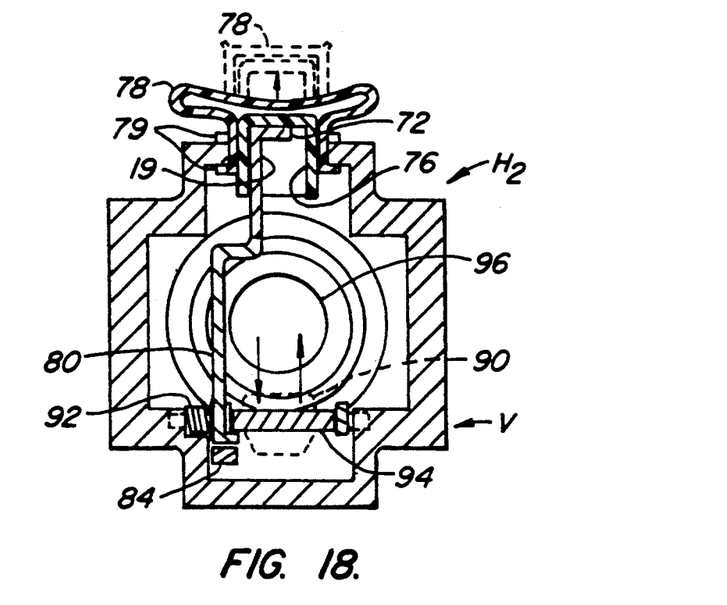
FIG. 18 is a front elevational view, with parts broken away and in cross-section illustrating the operation of the pushbutton valve actuator mechanism in the secondary housing.
Figure 19:
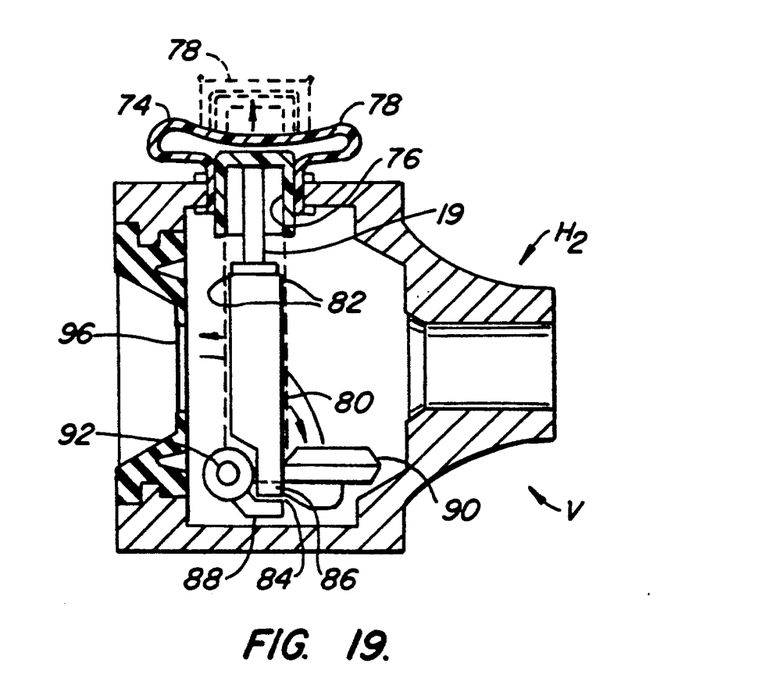
FIG. 19 is a side elevational cross-sectional view of the secondary housing further illustrating the operation of the pushbutton valve actuator mechanism.

FIGS. 18 and 19 show the pushbutton mechanism for actuating the flapper valve mechanism. A release plunger or actuation rod 19, which may be a metal stamping, is contained within secondary housing "H₂." The upper end 72 of rod 19 is bent at a right angle thereto and contacts the inner surface 74 of hollow, cylindrical injection-molded cup 76. Cup 76 is in turn contained within rubber pushbutton 78. Pushbutton 78 is of generally tubular configuration, having a closed and an open end. A pair of spaced circumferential ribs 79 adjacent the open end serve as a double baffle seal to prevent egress of gas from the secondary housing. The actuation rod 19 has a flared-out portion 80 intermediate its ends which is adapted to slide in grooves 82 molded within secondary housing "H₂." The pushbutton is located on the secondary housing at a location so as to be normally covered by the fingers, so that actuation requires little or no relocation of the hand.

The lower end of actuator rod 19 is bent to form a foot 84 which contacts the free end 86 of a lever 88 connected to one end of the flapper valve door 90 of valve mechanism "V." Pressing the pushbutton 78 as shown rotates the valve door 90 a full 90 degrees from its closed position to the fully open position shown against the biasing action of torsion spring 92. Torsion spring 92 acts on shaft 94, which is connected to valve door 90, and operates to normally close the door against an annular valve body seal 96 in the secondary housing "H₂." Shaft 94 is located entirely within secondary housing "H₂." In this manner, the shaft does not provide leakage paths to the exterior surrounds that might otherwise be the case if the shaft were mounted in holes drilled through to the exterior of the housing. The torsion spring has a force and the pushbutton a stroke sufficient to avoid accidental firing. Valve body seal 96 may be of soft rubber, while valve door 90 may be a lubricous injection-molded part.

OPERATION

Figure 6:
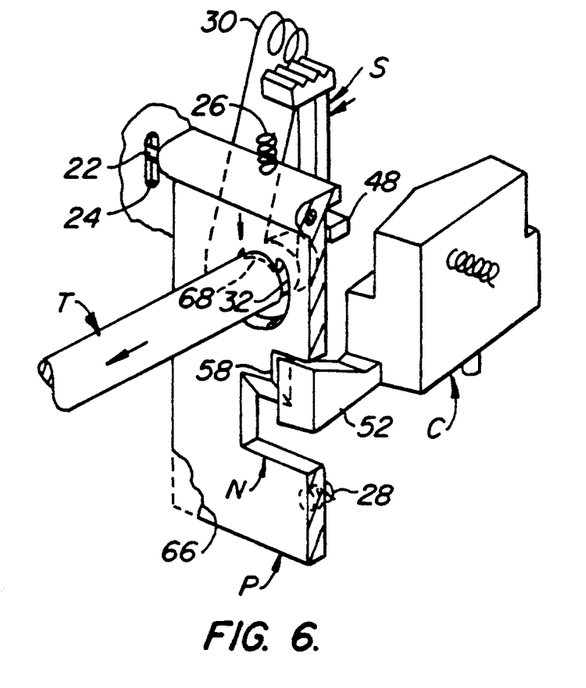
FIG. 6 is a perspective view similar to FIG. 2, showing the internal construction of the mechanism within the primary housing for the trocar assembly, with the trocar in the extended position at the commencement of penetration of body tissue.
Figure 7:
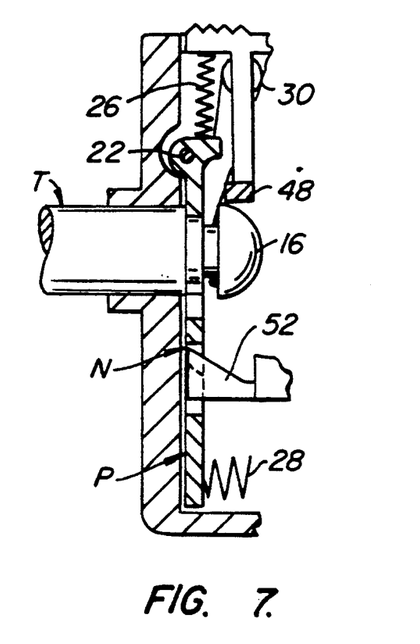
FIG. 7 is a cross-sectional side elevational view through the primary housing for the trocar assembly, with parts thereof broken away, illustrating the latching mechanism in the condition holding the trocar in the extended position shown in FIG. 6.

FIGS. 6 and 7 show the latching mechanism "cocked" to lock the trocar in the extended position. As there seen, the trocar has been slid forwardly by the slide "S," and the plate "P" has moved downwardly under the influence of the spring 26 to snap the extension 68 into engagement with the shoulder 70. These figures also show the cam arm "C" moved to the counterclockwise position with the side surface of the cam extension 52 in slidable engagement with the side surface 58 of the plate "P."

As conditioned in FIGS. 6 and 7, the trocar "T" is locked in a condition where its pointed tip 12 extends outwardly from the trocar tube 18 (see FIG. 1). As thus disposed, the trocar is conditioned to perform its piercing function.

Figure 8:
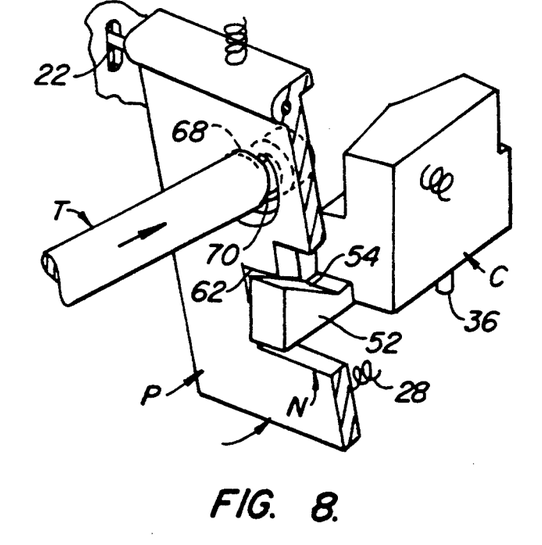
FIG. 8 is a perspective view similar to FIG. 6, showing the internal construction of the mechanism within the primary housing for the trocar assembly, with the trocar in the extended position applying pressure to the latching mechanism during the course of penetration of body tissue.
Figure 9:
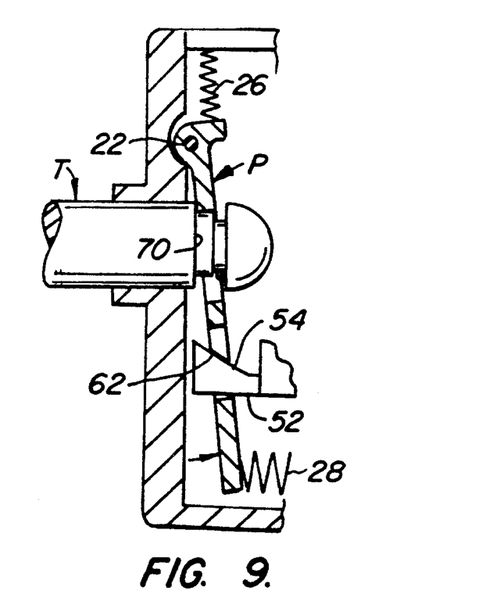
FIG. 9 is a cross-sectional side elevational view through the primary housing for the trocar assembly, with parts thereof broken away, illustrating the latching mechanism in the condition shown in FIG. 8.

FIGS. 8 and 9 show the latching mechanism as the trocar "T" initially encounters resistance upon the commencement of piercing. This resistance is depicted by the arrow marked on the trocar in FIG. 8. It functions to force the shoulder 70 into engagement with the extension 68 to pivot the plate "P" in a counterclockwise direction against the influence of the spring 28, without releasing the trocar from the extended position. Such pivoting functions to raise the notch "N" sufficiently to permit the cam extension 52 to move into the lateral extension 60 of the notch under the influence of the spring 40.

Figure 10:
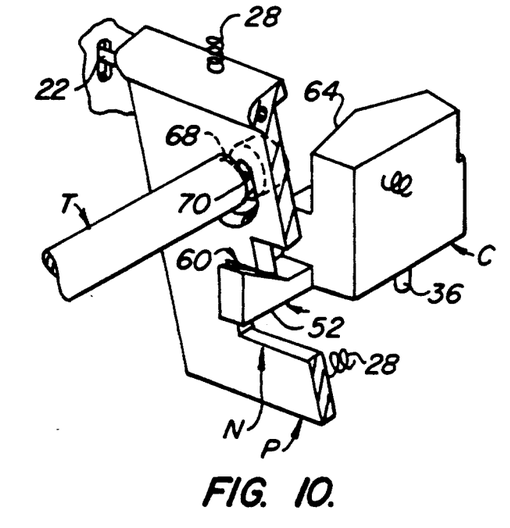
FIG. 10 is a perspective view similar to FIG. 8, showing the internal construction of the mechanism within the primary housing for the trocar assembly, with the trocar in the extended position and continuing to apply pressure to the mechanism during the course of penetration of body tissue.
Figure 11:
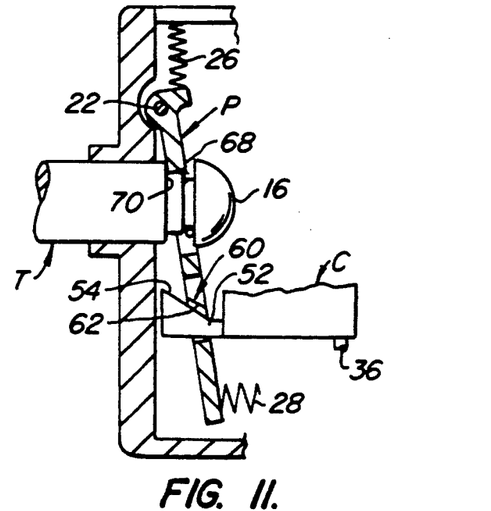
FIG. 11 is a cross-sectional side elevational view through the primary housing for the trocar assembly, with parts thereof broken away, illustrating the latching mechanism in the condition shown in FIG. 10.
Figure 12:
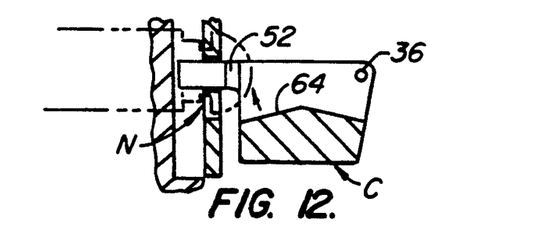
FIG. 12 is a cross-sectional plan view through the primary housing of the trocar assembly, illustrating the release cam of the latching mechanism in the condition shown in FIG. 10.

FIGS. 10, 11 and 12 depict the condition of the latching mechanism as pressure continues to be applied to the trocar during the piercing operation. As there shown, it will be seen that the shoulder 70 of the trocar remains in engagement with the detent extension 68 to maintain the trocar in the extended position, while the plate "P" has swung counterclockwise sufficiently to permit the cam extension 52 to fully enter the lateral section 60 of the notch "N."

Figure 13:
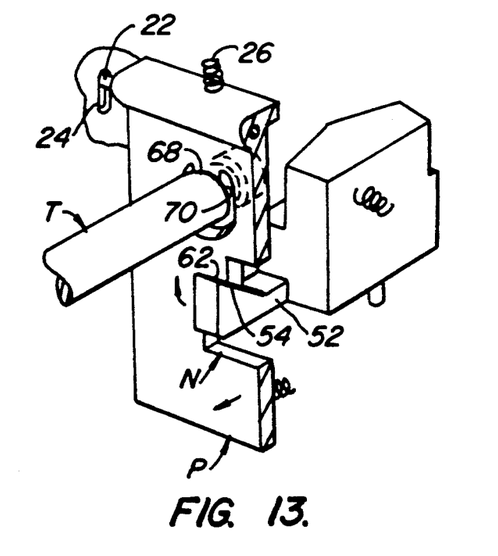
FIG. 13 is a perspective view similar to FIG. 10, showing the internal mechanism within the primary housing for the trocar assembly, with the trocar in the extended position as pressure is released at the completion of penetration of body tissue.
Figure 14:
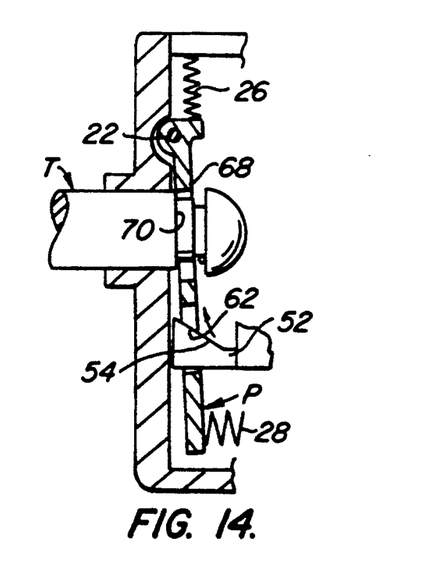
FIG. 14 is a cross-sectional side elevational view taken through the primary housing for the trocar assembly, with parts thereof broken away, illustrating the latching mechanism in the condition shown in FIG. 13.

FIGS. 13 and 14 show the latching mechanism at the instant piercing is completed and pressure is released from the trocar, thus permitting the plate "P" to move forwardly in a clockwise direction under the influence of the spring 28 and to slide upwardly under the camming influence of the cam surface 54 on the cam surface 62. Such upward movement moves the pins 22 upwardly in the grooves 24, and ultimately releases the detent extension 68 from the shoulder 70.

Figure 15:
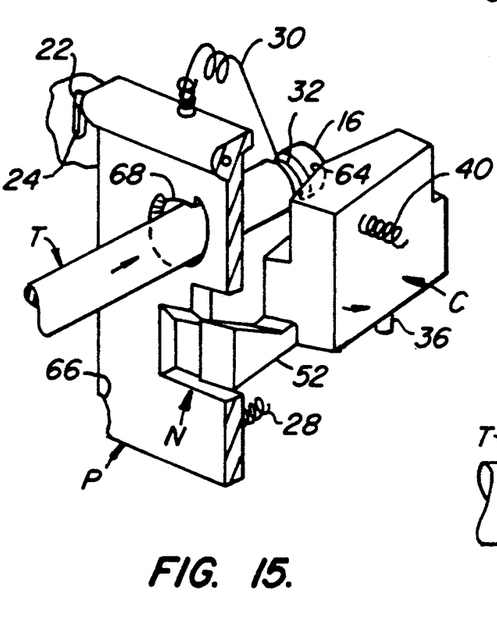
FIG. 15 is a perspective view similar to FIG. 13, showing the internal construction of the mechanism within the primary housing for the trocar assembly, with the trocar retracted after pressure has been released at the completion of penetration of body tissue.
Figure 16:
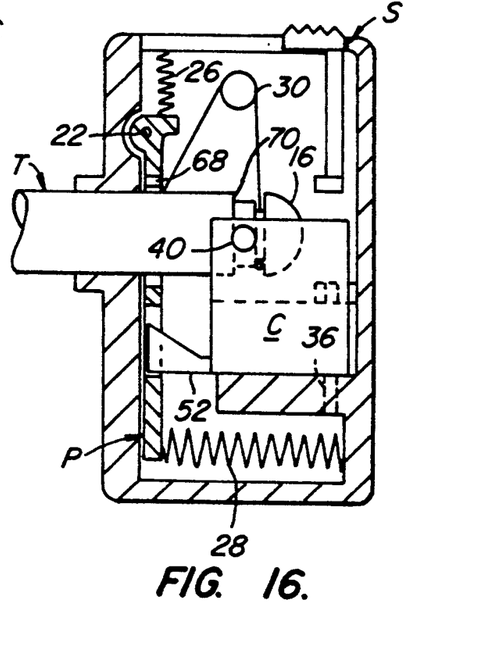
FIG. 16 is a cross-sectional side elevational view through the primary housing for the trocar assembly, with parts thereof broken away, illustrating the latching mechanism in the condition shown in FIG. 15.
Figure 17:
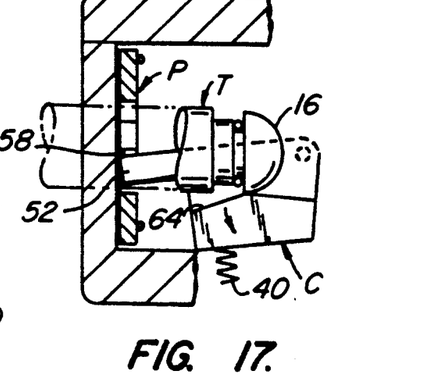
FIG. 17 is a cross-sectional plan view through the primary housing for the trocar assembly, illustrating the release cam of the latching mechanism in the condition shown in FIG. 15.

FIGS. 15, 16 and 17 show the latching mechanism at the termination of the piercing procedure when the detent extension 68 has fully disengaged from the shoulder 70 to release the trocar "T" for movement to the retracted position under the influence of the spring 30. As there shown, the plate "P" has moved to its full upward and clockwise position. These figures also show that during retraction, the hemispherical end 16 engages the cam surface 64 to move the cam arm "C" in a counterclockwise direction against the influence of the spring 40. Such movement, in turn, functions to move the extension 52 into the enlarged section 56 of the notch "N" in order that the side surface of the extension may engage with the side surface 58 of the notch "N." Thus, it will be appreciated that retraction of the trocar "T" functions to return the latching mechanism to the condition shown in FIGS. 1 to 4, wherein it may be re-cocked as shown in FIG. 6 for reuse.

It should be appreciated that the release steps shown in FIGS. 13 to 16 occur instantly upon the release of pressure from the trocar at the completion of its piercing function. This results in an instantaneous withdrawal of the trocar "T" into the trocar tube 18, and assures that inadvertent piercing of tissue will be avoided.

On completion of the desired piercing function, the primary housing "H₁" and attached trocar "T" may be withdrawn from the trocar tube 18, thus leaving the tube extended through the pierced tissue and into the body cavity desired to be accessed. As the trocar is fully withdrawn, the valve mechanism "V" closes, thus closing the passage through the tube 18. The valve may be selectively opened to provide access through the tube, either by the passage of instruments through the tube, or by manual actuation of the plunger 19 by depressing pushbutton 78. The pushbutton 78 may be easily manipulated by one hand so that the same hand can both hold the secondary housing "H₂" and open the valve therein by means of the pushbutton 78.

CONCLUSION

From the foregoing detailed description, it is believed apparent that the invention enables the attainment of the objects initially set forth herein. In particular, it provides a trocar which instantaneously retracts to a shielded condition upon the completion of the penetration of tissue. Simultaneously with such retraction, the mechanism of the trocar conditions itself for reuse.

It is to be understood that while the invention has been described above in conjunction with the preferred specific embodiments, the description and examples are intended to illustrate and not limit the scope of the invention, which is defined by the scope of the appended claims.

What is claimed is:

1. A trocar assembly comprising:
   (a) a primary base member;
   (b) an elongate trocar mounted on the primary member for movement between extended and retracted positions relative thereto, said trocar having a proximal portion received in the base member and a pointed distal portion extending from the base member for the application of piercing force;
   (c) biasing means to normally urge the trocar to the retracted position relative to the base member;
   (d) latch means within the primary base member engageable with the proximal portion of the trocar to secure the trocar in the extended position against the urging of the biasing means; and
   (e) release means within the primary base member for releasing the latch means upon the interruption of the application of piercing force to the distal portion of the trocar, wherein the release means includes a moveable member separate from the latch means.

2. An assembly according to claim 1 further comprising:
   (a) a secondary base member mutually engageable with the primary base member; and
   (b) a trocar tube carried by the secondary base member for slidably receiving the trocar upon mutual engagement of the primary and secondary base members to shield the distal portion when the trocar is in the retracted position and expose the distal portion when the trocar is in the extended position.

3. An assembly according to claim 2 wherein the secondary base member carries a valve to close the trocar tube when the trocar is removed from the tube.

4. An assembly according to claim 1 or 2 further comprising means responsive to movement of the trocar to the retracted position to condition the latch means for engagement with the trocar.

5. An assembly according to claim 1 wherein the primary base member carries means to selectively move the trocar to the extended position for engagement by the latch means.

6. An assembly according to claim 1, said trocar having a groove formed in the proximal portion thereof, said latch means comprising a plate carried by the primary base member for movement relative thereto between an extended condition engaged with said groove to secure the trocar in the extended position, and a retracted condition disengaged from the groove to release the trocar for movement by said biasing means.

7. An assembly according to claim 6 further comprising means to normally bias the plate to the extended condition.

8. An assembly according to claim 7 wherein the release means comprises a cam carried by the primary base member for movement between a first position disengaged from the plate and a second position disposed for engagement with the plate to move the plate to the retracted condition.

9. An assembly according to claim 8 wherein, upon movement to the retracted position, the trocar engages the cam to move the cam to the first position.

10. An assembly according to claim 9 further comprising a spring engaged between the primary base member and cam to normally bias the cam to the second position.

11. An assembly according to claim 1 wherein:
    (a) when the plate is engaged with the groove, piercing force applied to the distal portion of the trocar functions to move the plate relative to the primary base member; and
    (b) the release means functions in response to such movement.

12. An assembly according to claim 11 wherein the biasing means is engaged between the plate and the trocar to resist movement of the plate relative to the primary base member in response to piercing force applied to the distal portion of the trocar.

13. An assembly according to claim 12 further comprising means to normally bias the plate to the extended condition.

14. An assembly according to claim 13 wherein the latch means further comprises a release cam carried by the primary housing for movement between a first position disengaged from the plate and a second position disposed for engagement with the plate to move the plate to the retracted condition.

15. An assembly according to claim 14 wherein, upon movement to the retracted position, the trocar engages the cam to move the cam to the first position.

16. An assembly according to claim 15 further comprising a spring engaged between the primary housing and cam to normally bias the cam to the second position.

17. A trocar assembly comprising:
    (a) an elongate trocar received within a trocar tube for movement relative to the tube between a position extended from the tube for piercing and a retracted position shielded by the tube, said trocar having a groove formed in the proximal portion thereof;
    (b) a primary housing mounting the trocar for movement relative thereto between the extended and retracted positions;
    (c) biasing means carried by the housing to normally urge the trocar to the retracted position;
    (d) latch means within the housing engageable with the trocar to maintain the trocar in the extended position, said latch means being responsive to the application of piercing force to the trocar and functioning to release the trocar for retraction by the biasing means upon the interruption of such force; and (e) wherein the latch means comprises a plate carried by the primary housing for movement relative thereto between an extended condition engaged with the groove to secure the trocar in the extended position and a retracted condition disengaged from the groove to release the trocar for movement by the biasing means.

18. An assembly according to claim 17 wherein:
(a) the trocar tube is removable from the trocar and mounted on a secondary housing; and
(b) the primary and secondary housings are mutually engageable to maintain relative orientation of the trocar and tube when the trocar is received within the tube.

19. An assembly according to claim 18 wherein the secondary housing carries a valve to close the trocar tube when the trocar is removed from the tube.

20. An assembly according to claim 17 or 18 further comprising means responsive to movement of the trocar to the retracted position to condition the latch means for engagement with the trocar.

21. An assembly according to claim 17 wherein the primary housing carries means to selectively move the trocar to the extended position for engagement by the latch means.

22. An assembly according to claim 17 wherein:
(a) when the plate is engaged with the groove, piercing force applied to the trocar functions to move the plate relative to the primary housing; and
(b) the latch means functions in response to such movement to release the trocar for retraction upon the interruption of such force.

23. An assembly according to claim 22 wherein the biasing means is engaged between the plate and the trocar to resist movement of the plate relative to the primary housing in response to piercing force applied to the trocar.

24. An assembly according to claim 19 further including spring biasing means normally biasing said valve to the closed position, and manually operable pushbutton means on said secondary base member for actuating said valve to the open position.

25. An assembly according to claim 24 wherein said spring means is a spring, said valve further comprises a door mounted on a shaft, and wherein said shaft is pivotally mounted on said secondary base member.

26. An assembly according to claim 25 further including a lever connected to said shaft, and wherein said pushbutton means comprises an elongated release plunger slidably mounted in said secondary base member having one end in contacting relation to said lever and the other end operatively connected to a pushbutton on said secondary base member so that motion of said pushbutton is translated to said lever to rotate said door by means of said release plunger against the biasing action of said spring.

27. An assembly according to claim 17 or 18 wherein:
(a) said trocar is elongate and has a groove formed in the proximal portion thereof; and
(b) said latch means comprises a plate carried by the primary housing for movement relative thereto between an extended condition engaged with the groove to secure the trocar in the extended position and a retracted condition disengaged from the groove to release the trocar for movement by the biasing means.

28. A trocar assembly comprising:
a primary base member;
a trocar mounted on the primary base member;
a secondary base member mutually engageable with the primary base member;
a trocar tube carried by the secondary base member for receiving the trocar upon mutual engagement of the primary and secondary base members;
a valve in said secondary base member having spring biasing means thereon for closing the trocar tube when the trocar is removed from the tube; and
pushbutton means on said secondary base member for opening said valve and thereby opening access to said trocar tube;
wherein said spring means is a spring, and said valve further comprises a door and means pivotally connecting said door to said secondary base member;
wherein said means pivotally connecting said door to said secondary base member comprises a shaft pivotally mounted in said secondary base member, and wherein said door is mounted on said shaft;
wherein said pushbutton comprises a generally tubular boot open at one end, closed at the opposite end, and further including seal means for sealingly connecting said open end to said secondary base member.

29. An assembly according to claim 28 further including a lever connected to said shaft, and wherein said pushbutton means comprises an elongated release plunger slidably mounted in said secondary base member having one end in contacting relation to said lever and the other end operatively connected to a pushbutton on said secondary base member so that motion of said pushbutton is translated to said lever to rotate said door by means of said release plunger against the biasing action of said spring.

* * * * *